(12) United States Patent
Cummins et al.

(10) Patent No.: US 6,685,712 B2
(45) Date of Patent: Feb. 3, 2004

(54) SURGICAL MICRO-STAPLING INSTRUMENT

(76) Inventors: Christy Cummins, 54 Knockowen, Tullamore, County Offaly (IE); James Coleman, 20 Greenmount Road, Terenure, Dublin 6 (IE)

( * ) Notice: Subject to any disclaimer, the term of this patent is extended or adjusted under 35 U.S.C. 154(b) by 0 days.

(21) Appl. No.: 09/949,242

(22) Filed: Sep. 7, 2001

(65) Prior Publication Data

US 2002/0049455 A1 Apr. 25, 2002

(30) Foreign Application Priority Data

Sep. 8, 2000 (IE) .......................... S2000/0721

(51) Int. Cl.⁷ .......................... A61B 17/10; A61B 17/08
(52) U.S. Cl. .......................... 606/139; 606/142; 606/219
(58) Field of Search .......................... 227/24, 28, 175.1, 227/19, 151; 606/153, 139, 213, 219, 142

(56) References Cited

U.S. PATENT DOCUMENTS

| | | | |
|---|---|---|---|
| 3,601,302 A | * | 8/1971 | Potekhina et al. .......... 227/120 |
| 3,858,783 A | * | 1/1975 | Kapitanov et al. .......... 227/108 |
| 4,011,873 A | * | 3/1977 | Hoffmeister ................ 606/146 |
| 4,014,492 A | | 3/1977 | Rothfuss |
| 4,523,695 A | | 6/1985 | Braun et al. |
| 4,595,007 A | * | 6/1986 | Mericle ....................... 606/221 |
| 4,771,782 A | | 9/1988 | Millar |
| 4,789,090 A | | 12/1988 | Blake, III |
| 5,147,381 A | | 9/1992 | Heimerl et al. |
| 5,292,309 A | | 3/1994 | Van Tassel et al. |
| 5,292,332 A | | 3/1994 | Lee |
| 5,395,030 A | | 3/1995 | Kuramoto et al. |
| 5,431,639 A | | 7/1995 | Shaw |
| 5,470,010 A | | 11/1995 | Rothfuss et al. |
| 5,527,322 A | | 6/1996 | Klein et al. |
| 5,536,251 A | | 7/1996 | Evard et al. |
| 5,560,532 A | | 10/1996 | DeFonzo et al. |
| 5,643,318 A | | 7/1997 | Tsukernik et al. |
| 5,674,231 A | | 10/1997 | Green et al. |
| 5,810,846 A | | 9/1998 | Virnich et al. |
| 5,855,312 A | | 1/1999 | Toledano |
| 5,861,005 A | | 1/1999 | Kontos |
| 5,893,855 A | * | 4/1999 | Jacobs ........................ 606/150 |
| 6,446,854 B1 | * | 9/2002 | Remiszewski et al. ... 227/175.1 |

FOREIGN PATENT DOCUMENTS

| | | |
|---|---|---|
| EP | 0 386 361 | 9/1990 |
| EP | 0 756 851 | 2/1997 |
| EP | 0 774 237 | 5/1997 |
| EP | 0 941 697 | 9/1999 |
| WO | WO 97/20505 | 6/1997 |
| WO | WO 98/17179 | 4/1998 |
| WO | WO 98/25508 | 6/1998 |

* cited by examiner

*Primary Examiner*—Michael J. Milano
*Assistant Examiner*—Gwen Phanijphand
(74) *Attorney, Agent, or Firm*—Nutter, McClennen & Fish LLP

(57) ABSTRACT

A surgical stapling instrument for performing a vascular anastomosis procedure comprises an elongated body 10 and a needle 12 having a hook 12b for penetrating and everting the edges 56, 58 of tissue to be joined. The needle 12 is slidable in the body 10 between an extended position as shown and a retracted position wherein the hook is engaged with the end 10a of the body. A stapling mechanism includes a slidable pusher 40 for driving a staple 36 longitudinally of the body 10 against the inside of the hook 12b for deformation of the staple into penetrating engagement with the everted tissue edges 56, 58.

12 Claims, 10 Drawing Sheets

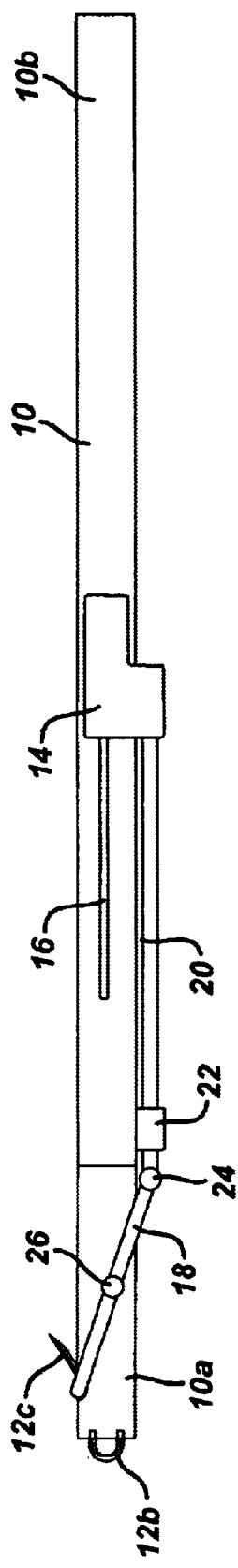
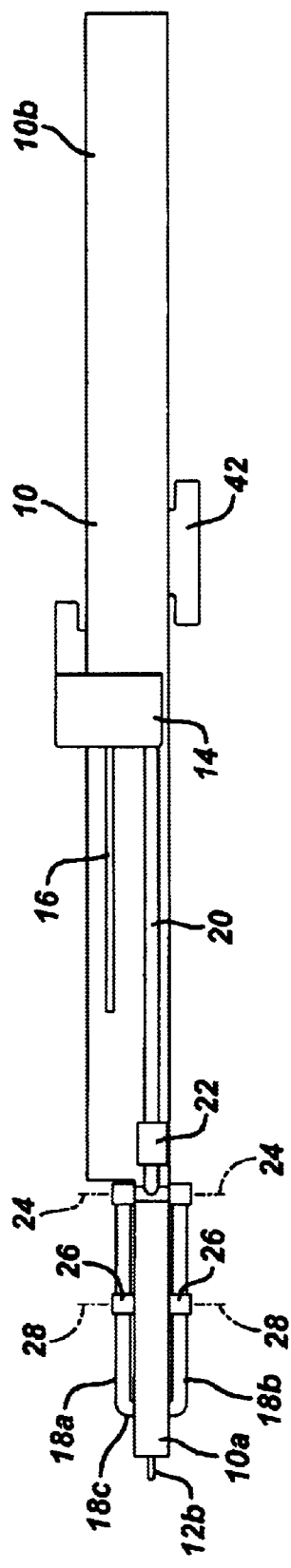
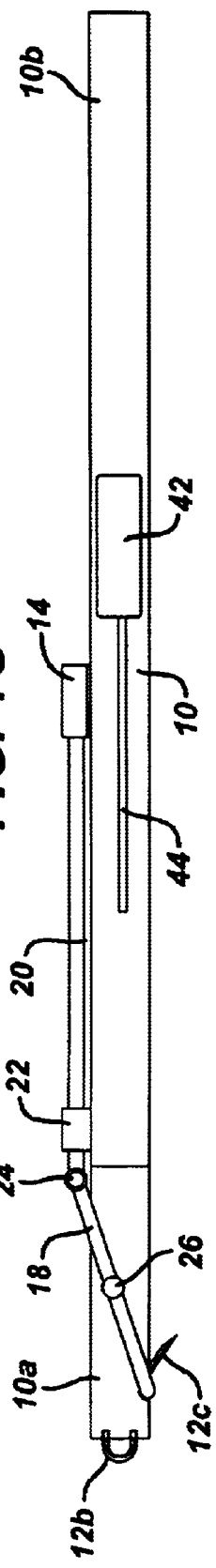

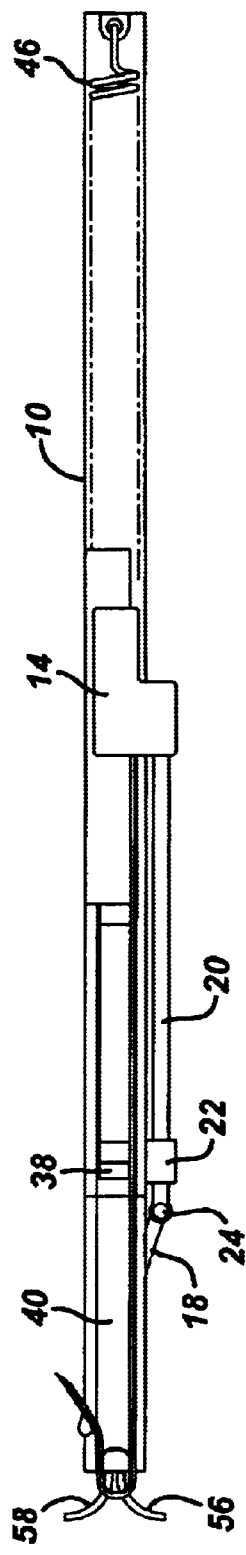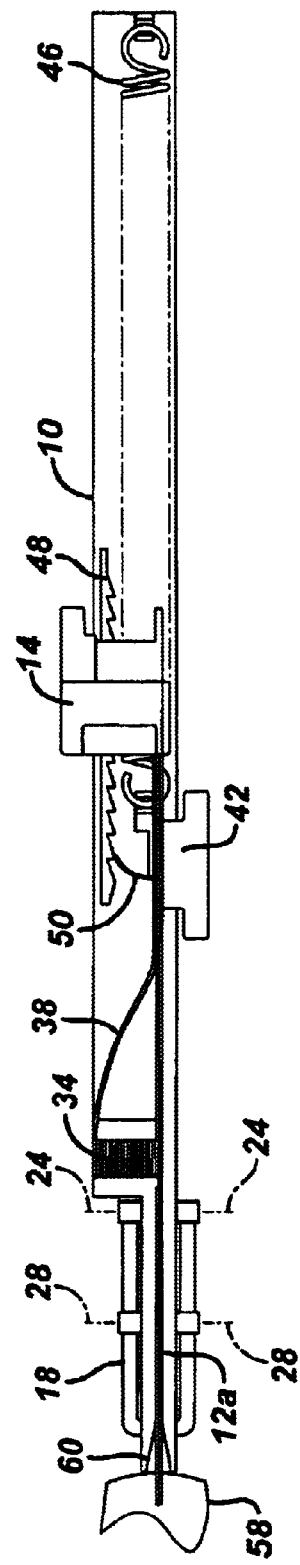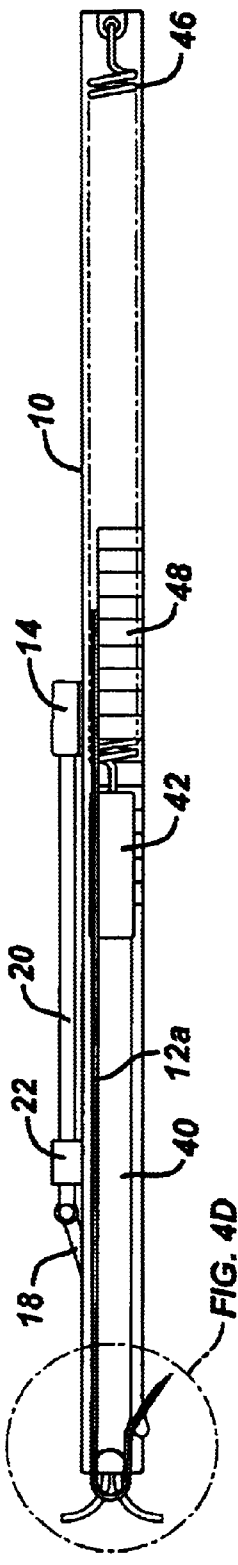

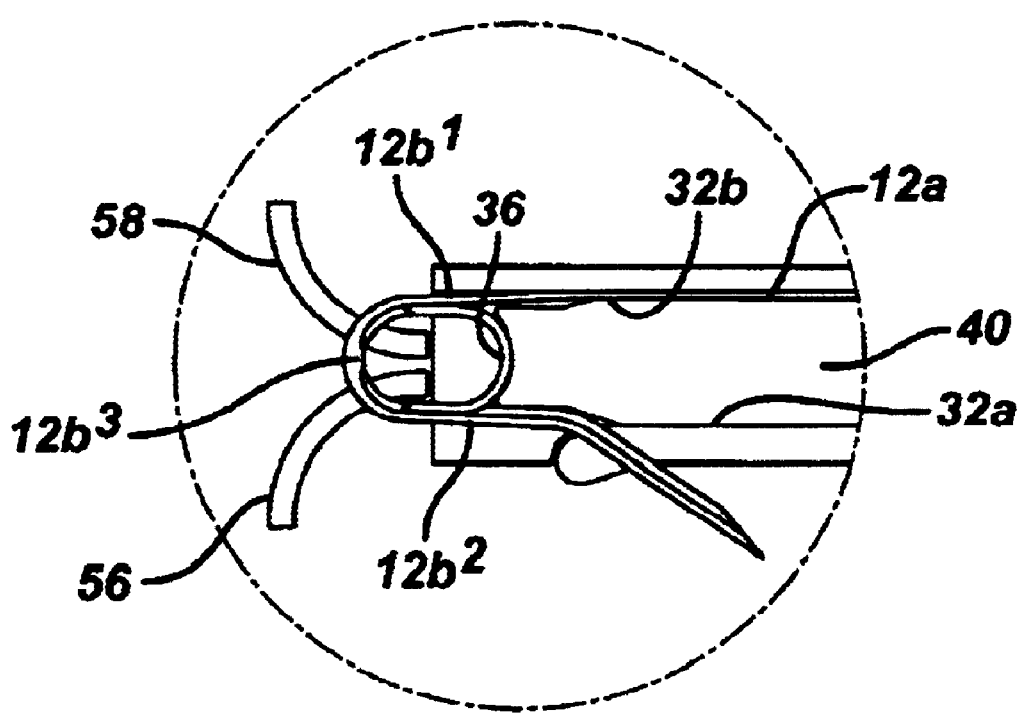

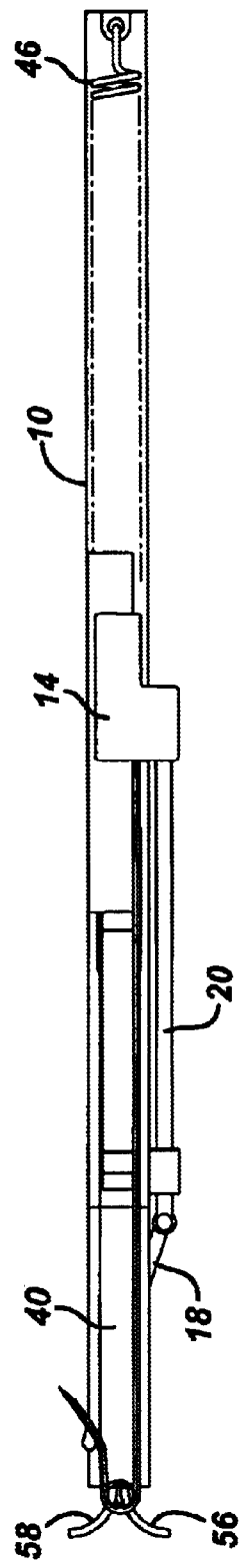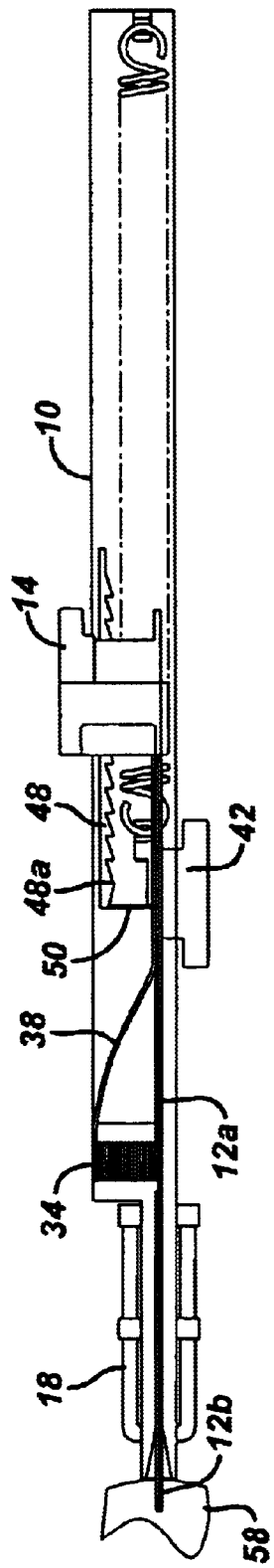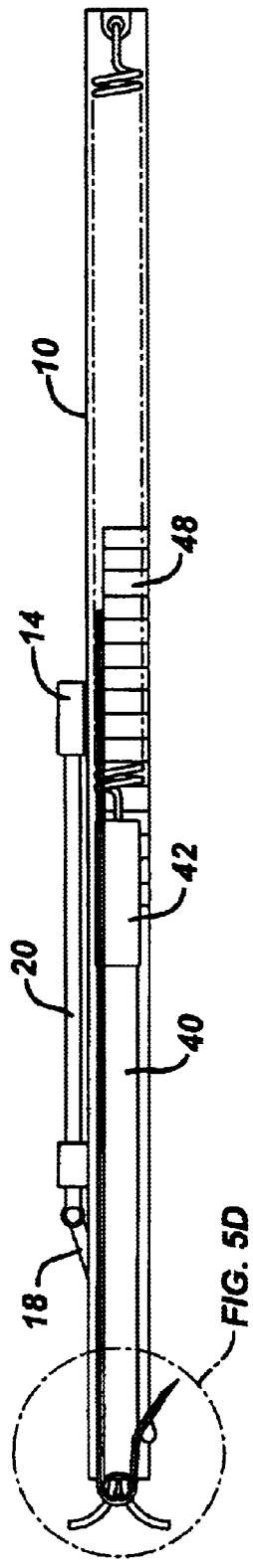

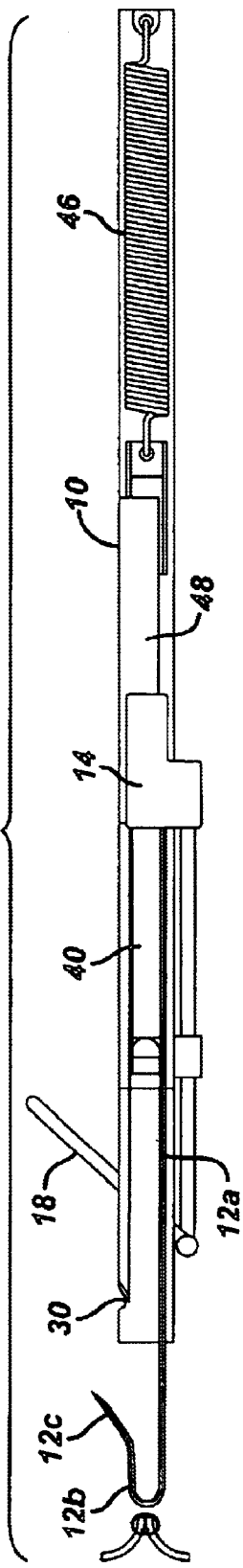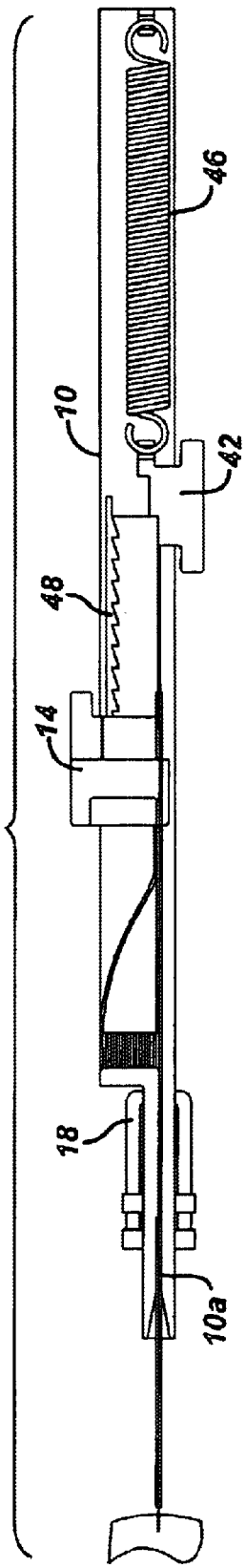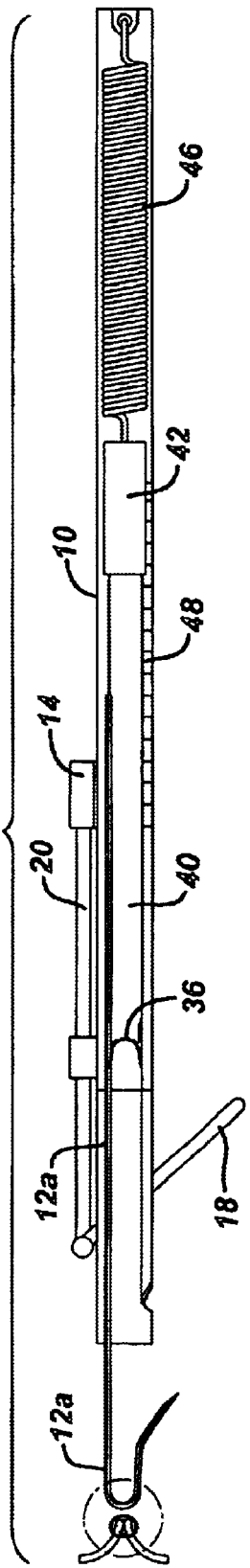

SURGICAL MICRO-STAPLING INSTRUMENT

FIELD OF THE INVENTION

The present invention relates to surgical stapling instruments, and in particular to instruments for performing a vascular anastomosis procedure.

BACKGROUND OF THE INVENTION

The term "anastomosis" covers a variety of procedures in which blood vessels such as veins and arteries, or other tubular members, such as part of the colon, intestines, stomach etc., are joined or reconnected. These vessels may be joined in a variety of relative orientations, including end-to-end and end-to-side and side-to side.

Recent advances made in the field of microsurgery and beating heart surgery have led to the development of alternatives to conventional suturing processes for joining vessels in order to accommodate the minute size of the vessels and in particular towards achieving a rapid anastomosis during beating heart (off-pump) coronary artery bypass surgery.

An alternative to suturing is the use of surgical clips which are applied along the junction between the vessels or tissue portions which are to be joined, and the clips perform a holding function similar to that of sutures. Two such non-penetrating clips are shown in U.S. Pat. Nos. 4,586,503 and 4,733,664.

The former patent discloses a surgical micro clip composed of plastically deformable metal or plastic material having minimal spring back when crimped. The clip has a pair of parallel curved legs joined by a bridge at one end and terminating in round tips at the other end. The clip grips the edges of the everted tissue and joins them by crimping the legs together.

The latter patent discloses a vascular surgical clip comprising a plastically deformable body portion, a tang for deforming the body, and the neck connecting the tang to the body. The body is designed to deform upon application to the tang of a predetermined tensile force, and the neck is designed to break upon application of a force in excess of the predetermined force to the tang.

As described in the above patents, the non-penetrating clips are applied over opposed edges of the vessels, the edges being first everted, or turned outward, to form flanges that are gripped between the jaws of the clips. A disadvantage of the above non-penetrating clip is the necessity to apply these clips to the outside of the everted tissues. The anastomosed vessels being repaired need to be returned to the intended function as quickly as possible, particularly where critical blood flow is involved.

The need therefore, exists for an instrument for rapidly applying surgical staples from either within the lumen or from outside the site of the anastomosis.

SUMMARY OF THE INVENTION

Accordingly, the present invention provides a surgical stapling instrument for stapling edges of tissue to be joined, the instrument comprising an elongated body and, carried by the body, a rigid member having a hooked end for penetrating the edges of tissue to be joined and stapling means for applying a staple to the edges held by the hooked end of the rigid member.

The invention also provides a device which accomplishes the same result with folds in tissue, i.e. rather than stapling two edges of tissue, an unbroken area of tissue may be folded and the folds stapled together in the same manner.

Preferably the stapling means comprises means for driving a staple longitudinally of the body against the inside of the hooked end of the needle for deformation of the staple into penetrating engagement with the everted edges.

The present invention may be used to perform a variety of vascular anastomosis including peripheral vascular surgical anastomosis, arterial venous fistula formation for dialysis, and coronary artery bypass anastomosis. More particularly, the present invention may be used to perform a coronary artery bypass anastomosis utilising a number of approaches including an open-chest approach (with and without cardiopulmonary bypass), a closed-chest approach under direct viewing and/or indirect thorascopic viewing (with and without cardiopulmonary bypass).

In an embodiment of the invention the instrument includes an elongated body with a handle at one end (herein referred to as the rear end) and which terminates at the other (front) end in a vascular staple delivery mechanism and a tissue grasping needle having a sharp hooked end. The elongated body portion includes two manually slidable members, the first to extend and retract the needle relative to the front end of the body and the second to deliver a staple which is deformed around an anvil on the inside of the hooked end of the needle. The staple is advanced by a spring biased pusher member coupled to the second slider.

Upon approximation of one of the tissue walls to be anastomosed by a suitable vascular forceps, the needle is extended so that the sharp hooked end of the needle is advanced free of the front end of the body so that, by manipulation by the user, it can penetrate and hook the tissue wall. When one tissue wall has been hooked, the forceps are used to approximate the other tissue wall which is then also hooked by the extended needle. The needle is configured so that when the tissue wall has been hooked it is inclined to slide back towards the narrow hooked end. The width of the hooked end is optimally equivalent to the combined wall thicknesses of the tissue walls being anastomosed. The needle is then retracted so that the hooked end grasping the tissue walls engages the front end of the body for stability during the subsequent staple delivery.

Once the tissue to be anastomosed has been grasped and approximated against the front end of the body the pusher member is advanced forwardly along a track in which a staple from a stack of 20 or more is positioned. The pusher member advances the staple along the track until the staple legs engage the inside edge of the hooked end of the needle. As the staple is further advanced the legs are deformed inward and toward each other by the anvil through the hole in the tissue walls created by the needle. Once the staple is deployed the pusher member returns so that its front end is positioned proximal to the staple stack.

The needle slider is then advanced so as to move the needle and stapled tissue away from the front end of the body to allow the needle to be unhooked from the stapled tissue.

In a further aspect the invention provides a method of stapling the edges of tissue to be joined, comprising the steps of:
a) penetrating the edges of tissue to be joined with a rigid member having a hooked end; and
b) applying a staple to the edges held by the hooked end of the rigid member.

BRIEF DESCRIPTION OF THE DRAWINGS

The embodiment of the invention will now be described, by way of example, with reference to the accompanying drawings, in which:

FIGS. 1A to 1C are, respectively, a side view, a top plan view and an opposite side view of an instrument for applying a surgical staple to a blood vessel during a microsurgical anastomosis procedure;

FIGS. 4A to 4C are longitudinal sectional views of the instrument, similar to those of FIGS. 2A to 2C, showing a staple driven forwardly into the hook of the needle just prior to closing the staple onto the tissue;

FIG. 4D is an enlarged detailed view of the circled part of FIG. 4C;

FIGS. 5A to 5C are longitudinal sectional views of the instrument, similar to those of FIGS. 2A to 2C, just after closure of the staple;

FIGS. 6A to 6C are longitudinal sectional views of the instrument, similar to those of FIGS. 2A to 2C, with the needle extended once again to release the stapled tissue;

DETAILED DESCRIPTION OF THE PREFERRED EMBODIMENTS

Figure 2A:
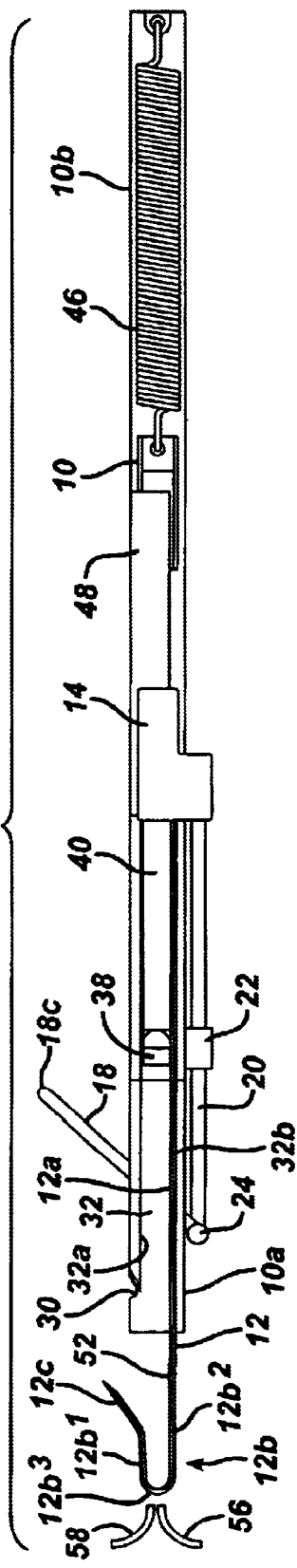
FIGS. 2A to 2C are longitudinal sectional views of the instrument, similar to those of FIGS. 1A to 1C, with the needle extended in preparation for penetrating and grasping the edges of tissue to be anastomosed.

Referring now to the drawings, an instrument for applying a surgical staple to a blood vessel during a microsurgical anastomosis procedure comprises an elongated hollow body 10 having a front "business" end 10a and a rear handle end 10b. A needle 12 is mounted within the body 10 and has a straight body portion 12a and a hooked front end 12b (hereinafter referred to simply as a hook), the hook 12b terminating in a sharp outwardly inclined tip 12c.

Figure 5D:
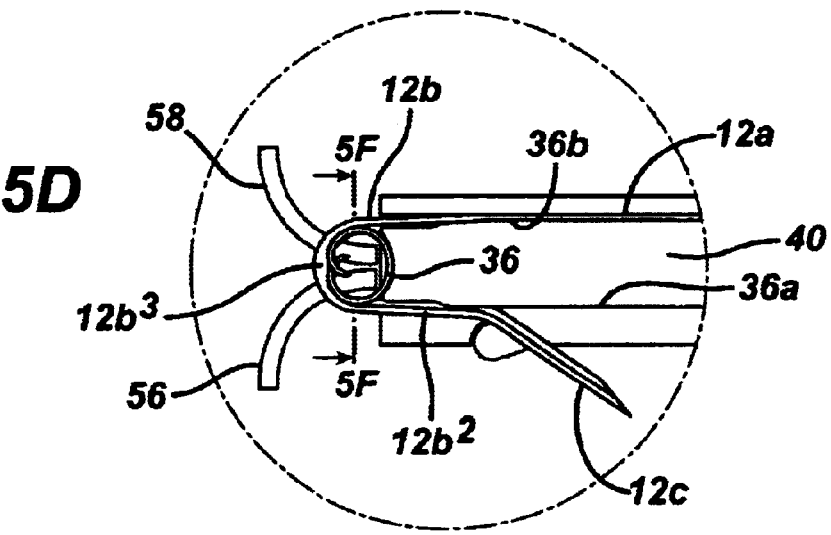
FIG. 5D is an enlarged detailed view of the circled part of FIG. 5C.
Figure 5E:
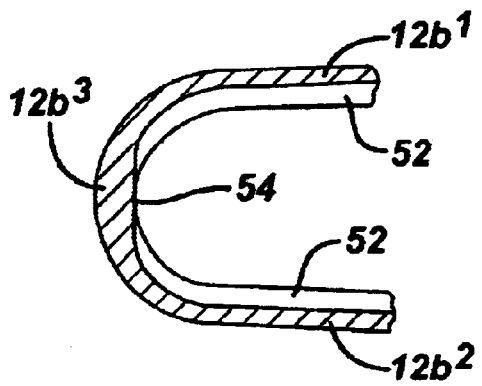
FIG. 5E is an enlarged detailed view of the circled part of FIG. 5D.
Figure 5F:
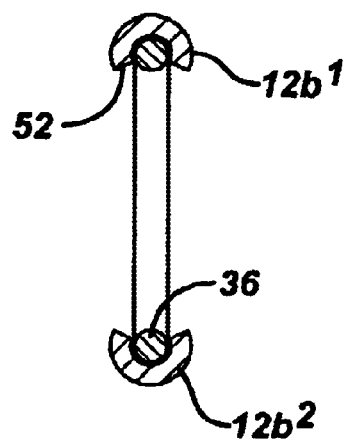
FIG. 5F is an enlarged cross-section taken on the line A—A of FIG. 5D.
Figure 6D:
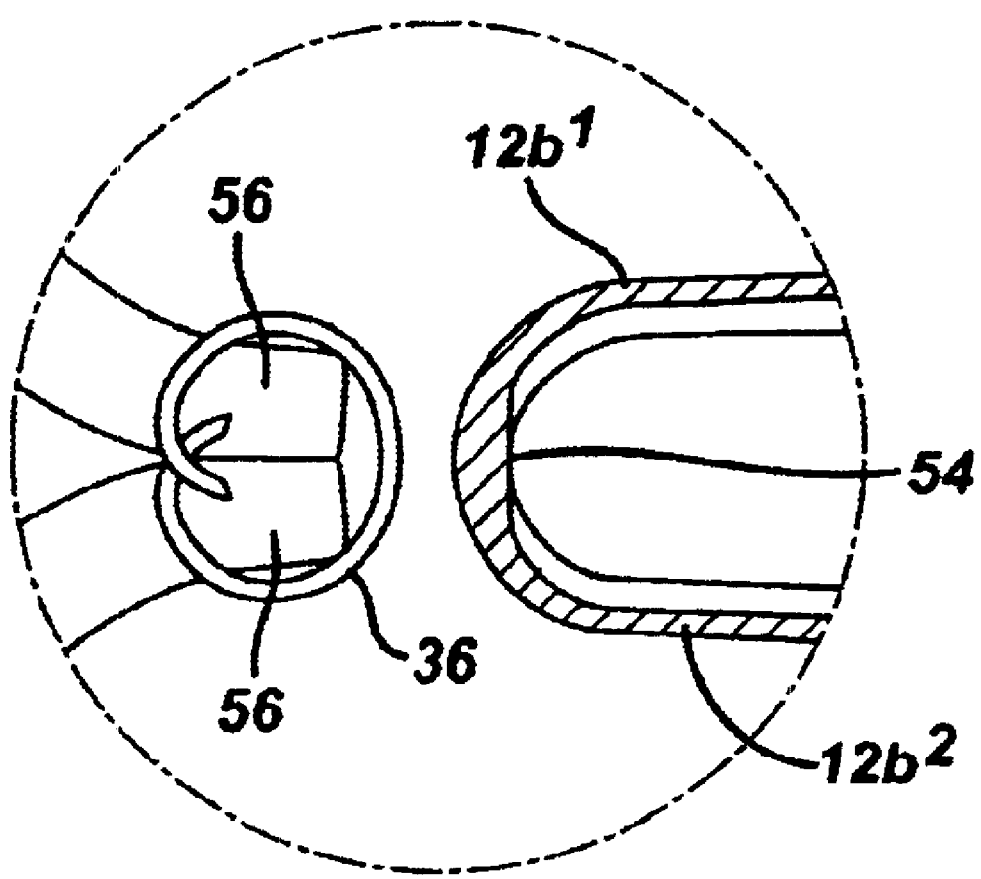
FIG. 6D is an enlarged detailed view of the circled part of FIG. 6C.

The body portion 12a of the needle is parallel to the longitudinal axis of the body 10 and is slidable longitudinally of the body 10 between an extended position, FIGS. 2 and 6, wherein the hook 12b is free of the front end 10a of the body 10 and a retracted position, FIGS. 1, 3, 4 and 5, wherein the opposite sides $12b^1$ and $12b^2$ of the hook are engaged with the front end 10a of the body.

The needle 12 is actuated between its extended and retracted positions by a thumb-operated slider 14 mounted on the outside of the body 10 and fixed to the rear end of the needle portion 12a through a longitudinal slot 16 (FIG. 1A) in the body. In its extended position the needle 12 is able to penetrate and evert tissue walls to be anastomosed, while in its retracted position the needle allows a staple to be delivered to the everted tissue walls, as will be described.

The slider 14 also operates a needle lock 18 via a push rod 20 which is slidable longitudinally of the body 10 in a bearing 22. The needle lock comprises a U-shaped member 18 which embraces the front end 10a of the body 10 and whose opposite arms 18a, 18b are pivoted to the front end of the push rod 20 for rotation about an axis 24 normal to the axis of the body 10. The arms 18a, 18b also slide in respective bearings 26 which are mounted on opposite sides of the front end 10a of the body 10 for rotation about an axis 28 parallel to the axis 24.

When the needle 12 is fully retracted (FIGS. 1, 3, 4 and 5) the base 18c of the U-shaped member 18 engages in a groove 30 in the front end 10a of the body 10 just behind the needle tip 12c.

This maintains the inside edge of the side $12b^1$ of the hook in alignment with one edge 32a of a narrow staple guide slot 32 in the body 10, the straight portion 12a of the needle extending along the opposite edge 32b of the guide slot. As will be described, this provides continuous guidance for a staple along the guide slot 32, out of the front end 10a of the body 10 and between the opposite sides $12b^1$ and $12b^2$ of the hook fully to the curved base $12b^3$ of the hook.

When the slider 14 is pushed forwardly to extend the needle 12, the push rod 20 pushes the pivot axis 24 forwardly so that the U-shaped member 18 rotates and slides in the bearings 26 so that it is lifted out of the groove 30 to allow free forward movement of the tip 12c of the needle, FIGS. 2 and 6.

Figure 2B:
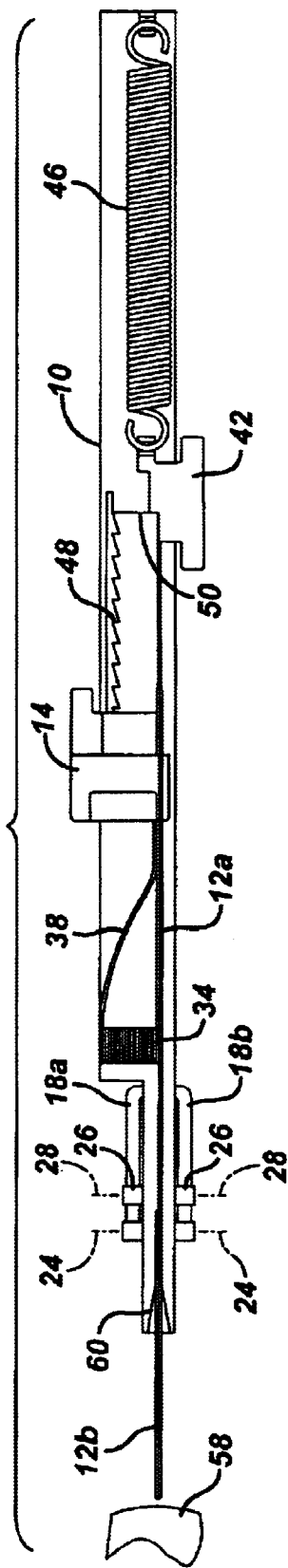
Figure 2C:
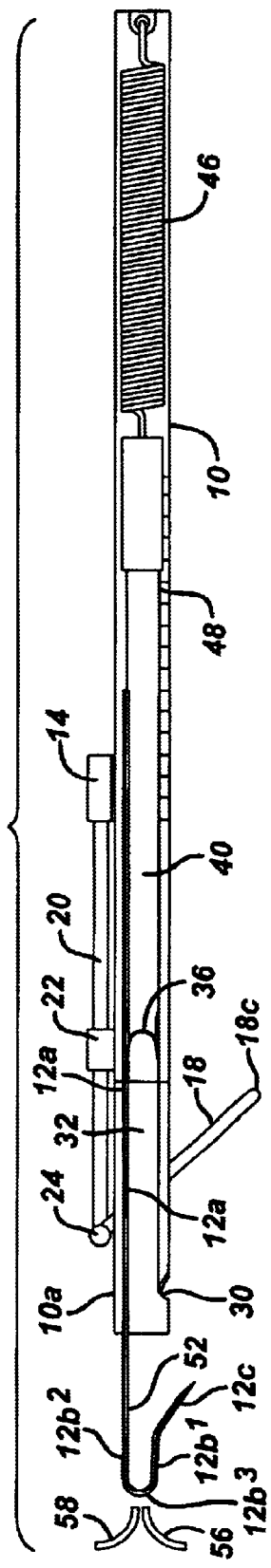
Figure 3A:
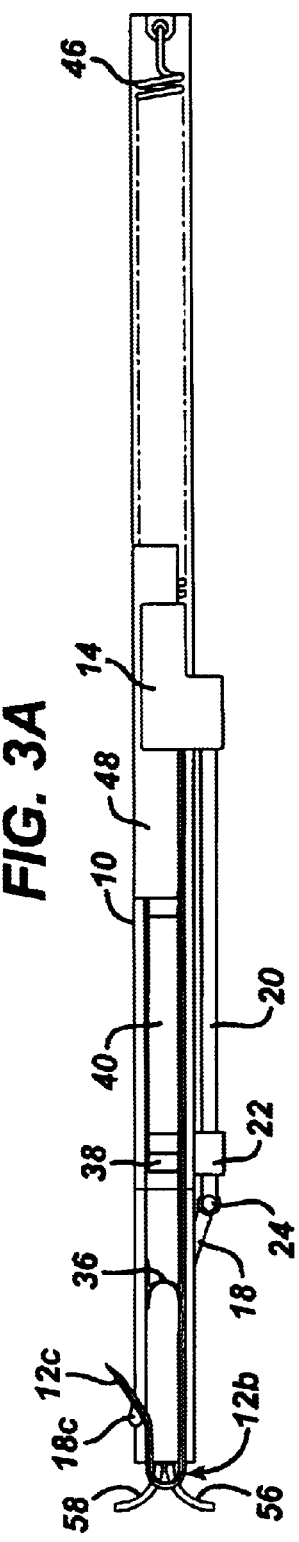
FIGS. 3A to 3C are longitudinal sectional views of the instrument, similar to those of FIGS. 2A to 2C, with the needle retracted after having penetrated and grasped the edges of the tissue.
Figure 3B:
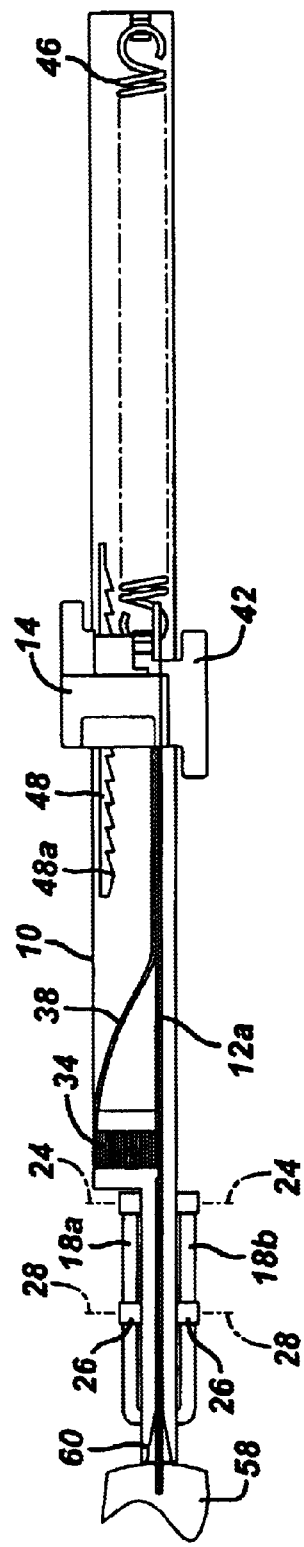
Figure 3C:
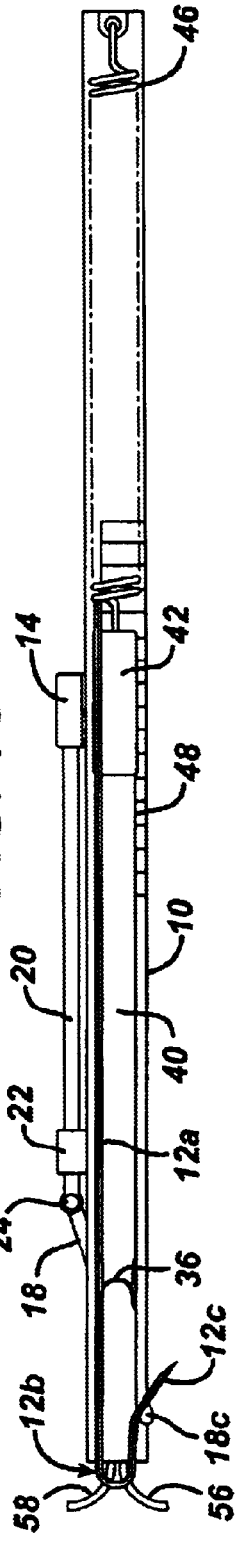

A stack 34 of staples 36 are accommodated in the body 10, the stack 34 being pressed laterally towards the guide slot 32 by a leaf spring 38 so that the lowermost staple in the stack (as seen in FIG. 2B) is aligned with the staple guide slot 32 with its legs pointing forward (FIG. 2C).

Staples are contained in a removable cartridge-like housing. When the contents of the cartridge have been exhausted, the empty cartridge is ejected from the device and replaced with a new cartridge pre-loaded with the desired quantity of staples.

A staple pusher 40 is slidable in the guide slot 32 behind the staple 36, so that, when the needle 12 is fully retracted, by sliding the pusher 40 forwardly the staple 36 currently aligned with the slot 32 is pushed forwardly along the slot, toward the forward end 10a of the body 10, between the opposite sides $12b^1$ and $12b^2$ of the hook 12b and finally up against the curved base $12b^3$ of the hook. The pusher 40 is actuated by a further thumb-operated slider 42 mounted on the outside of the body 10 and fixed to the rear end of the pusher 40 through a further longitudinal slot 44 (FIG. 1C) in the body.

The slider 42 is coupled to the rear end 10b of the body 10 by a tension spring 46 which biases the pusher 40 towards the rear end 10b. Therefore, the user has to push against the bias of the spring 46 when advancing the pusher 40. However, a ratchet 48 engaged by a ratchet spring 50 fixed to the slider 42 ensures that the pusher 40 cannot inadvertently return towards the rear end 10b of the body 10 until a full forward stroke of the pusher 40 has been completed, at which point the ratchet spring disengages from the front end 48a of the ratchet 48 (FIG. 5B) to allow return of the pusher.

Except at the curved base $12b^3$ of the hook 12b the needle 12 has a generally C-shaped cross-section along its full length. This defines a channel 52 along the inside edge of the needle 12. When the needle 12 is fully retracted and a staple 36 is pushed forwardly by the pusher 40 as described, within the body 10 the staple is guided towards the hook 12b by sliding along the slot 32 with one leg of the staple engaging in the channel 52 in the straight portion 12a of the needle and the other leg of the staple engaging the edge 32a of the slot.

When the staple 36 leaves the front end 10a of the body 10 the leg previously engaging the edge 32a of the slot 32 now enters and slides along the channel 52 in the side 12b$^1$ of the hook which is held in alignment with the edge 32a by the needle lock 18. At the same time the other leg of the staple 36 continues along the channel 52 in the side 12b$^2$ of the hook (FIGS. 5E and 5F).

At the curved base 12b$^3$ of the hook 12b the inside edge of the needle has an anvil bump 54, FIG. 5E. As a staple 36 is driven up against the base 12b$^3$ of the hook by the pusher 40, the legs of the staple are deformed so that they close to penetrate the everted tissue walls held by the hook 12b (FIG. 5D).

In use of the instrument, one of the tissue walls 56 to be anastomosed is grasped by a suitable vascular forceps. Then the needle 12 is extended so that the needle lock 18 is rotated out of the groove 30 and the hook 12b is advanced free of the front end 10a of the body 10 (FIG. 2) so that, by manipulation by the user, it can penetrate and hook the tissue wall 56. When one tissue wall has been hooked, the forceps are used to grasp the other tissue wall 58 which is then also hooked by the extended needle.

The needle is manipulated so that the hooked tissue flaps slide toward the curved base. The needle 12 is then retracted so that the hook 12b engages the front end 10a of the body 10 and the needle lock 18 rotates back into the groove 30, FIG. 3. It will be noted that retraction of the needle automatically everts the tissue walls 56, 58. The front end 10a of the body 10 has a V-shaped slot 60 which guides the side 12b$^1$ of the hook to its final position in alignment with the edge 32a of the slot 32.

Now the pusher 40 is advanced forwardly to drive the lowermost staple 36 in the stack 34 along the track 32 until the staple legs engage the channel 52 in the inside edges of the opposite sides 12b$^1$ and 12b$^2$ of the hook 12b, FIG. 4. As the staple is further advanced its legs are deformed inward and toward each other by the anvil bump 54 so that the legs of the staple pass through the holes in the tissue walls 56, 58 created by the needle 12, FIG. 5. Once the staple is deployed the pusher 40 returns so that its front end is once more positioned behind the staple stack 34 ready for a future deployment.

The needle slider 14 is then advanced so as to move the needle hook 12b and stapled tissue away from the front end 10 of the body 10 to allow the needle 12 to be unhooked from the stapled tissue, FIG. 6.

The staple is made from a biocompatible material such as titanium or stainless steel. Specialist materials such as nitinol (memory metal) may also be used. Typically the material used will be ductile, easily formed, and will have minimum spring back. Preferably, the staple will be generally U-shaped with a curved base and straight sides, the sides being angled outward with respect to its centre-line. When loaded in the cartridge, the legs are compressed inwards until approximately parallel with the centre-line. This outward bias on the legs ensures they remain stacked tightly in position within the cartridge and prevents inadvertent forward movement of the staple when advancing along guide slot 32.

While the staple legs are preferably pointed as shown, pointed ends are not necessarily required as the tissue grasping needle will already have punctured the tissue when the staple is deployed.

In another embodiment an adjustment feature is added to the device which allows the user to vary the forward movement of the staple pusher 40. It can be seen that advancing the pusher beyond its normal stop will close the staple further. This has advantage where the user finds that the factory setting is insufficient to form a tight anastomosis. The device can then be adjusted to allow the staple pusher 40 advance further thereby closing the staple more tightly and providing a better quality anastomosis.

Figure 7:
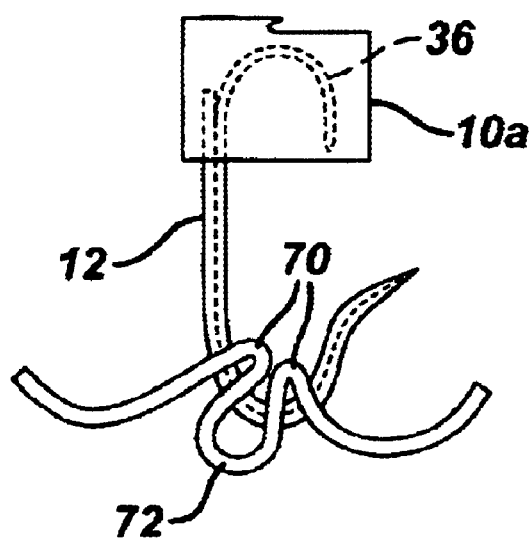
FIG. 7 is a schematic side view of the tip of the instrument during the creation of a pleat in tissue.
Figure 8:
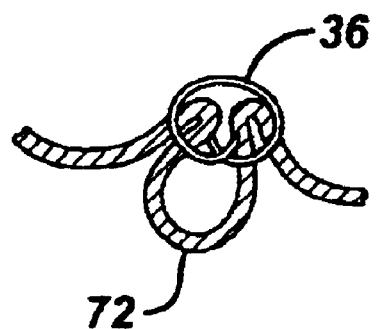
FIG. 8 is a sectional side view of the pleat when created by the instrument.

In another application the device may be used to create folds or pleats in tissue. An example of this is the creation of folds at the gastro-oesophagal junction as a possible cure of gastro-oesophagal reflux disease (GERD). In this instance, as illustrated in FIG. 7, the needle 12 is displaced forward from the front end 10a of the stapler and is used to penetrate a pair of convex tissue folds 70 defining a concave fold 72 between them. A staple 36 is then applied onto the needle 12 in the manner described previously, and the staple deformed as shown in FIG. 8 to capture the concave fold 72.

The invention is not limited to the embodiment described herein which may be modified or varied without departing from the scope of the invention.

What is claimed is:

1. A surgical stapling instrument for stapling edges of tissue to be joined, the instrument comprising an elongated body and, carried by the body, a rigid member having a hooked end for penetrating the edges of tissue to be joined and stapling means for applying a staple having opposed legs to the edges held by the hooked end of the rigid member such that each leg penetrates an edge of tissue and substantially simultaneously deforms toward one another against the hooked end to join the edges of tissue.

2. The instrument of claim 1, wherein the stapling means comprises means for driving a staple longitudinally of the body against an inside of the hooked end of the rigid member for deformation of the staple into penetrating engagement with the edges.

3. The instrument of claim 2, wherein an inner edge of the rigid member has a channel which provides a guide track for the staple.

4. The instrument of claim 3, wherein the rigid member has a substantially straight portion extending into the body with said hooked end being formed at one end of the straight portion, wherein within the body the staple is guided towards the hooked end by sliding along a slot in the body with one leg of the staple engaging the channel in the straight portion of the rigid member, and wherein within the hooked end of the rigid member the staple is guided by sliding engagement of the opposite legs of the staple with the channels in the opposite sides of the hooked end respectively.

5. The instrument of claim 4, wherein the rigid member is slidable longitudinally of the elongated body between an extended position wherein the hooked end is free of the said end of the body for penetrating the edges of a wound and a retracted position wherein opposite sides of the booked end are engaged with the body to allow the staple to be driven against the inside of the hooked end, the stapler further including means for sliding the rigid member between the extended and retracted positions.

6. The instrument of claim 5, wherein each of the rigid member sliding means and staple driving means comprises a respective manually operable slider mounted on the body.

7. The instrument of claim 6, wherein said rigid member is a curved needle.

8. The instrument of claim 7, wherein said rigid member is operable to evert the edges of the tissue as they are penetrated.

9. The instrument of claim 2, wherein the degree of staple deformation can be adjusted.

10. A method of stapling the edges of tissue to be joined, comprising the steps of:
   a) penetrating the edges of tissue to be joined with a rigid member having a hooked end; and
   b) applying a staple having opposed legs to the edges held by the hooked end of the rigid member such that each leg penetrates an edge of tissue and substantially simultaneously deforms toward one another against the hooked end to join the edges of tissue.

11. A surgical stapling instrument for stapling folds of tissue to be joined, the instrument comprising an elongated body and, carried by the body, a rigid member having a hooked end for penetrating the folds of tissue to be joined and stapling means for applying a staple having opposed lees to the folds by the hooked end of the rigid member such that each leg penetrates a fold of tissue and substantially simultaneously deforms toward one another against the hooked end to join the folds of tissue.

12. A method of stapling folds of tissue to be joined, comprising the steps of:
   a) penetrating the folds of tissue to be joined with a rigid member having a hooked end; and
   b) applying a staple having opposed legs to the folds held by the hooked end of the rigid member such that each leg penetrates a fold of tissue and substantially simultaneously deforms toward one another against the hooked end to join the edges of tissue.

* * * * *